(12) United States Patent
Mathiowitz et al.

(10) Patent No.: US 6,475,779 B2
(45) Date of Patent: *Nov. 5, 2002

(54) POLYMERIC GENE DELIVERY

(75) Inventors: Edith Mathiowitz, Brookline, MA (US); Yong Shik Jong, Seoul (KR); Kim Boekelheide, Wakefield, RI (US)

(73) Assignee: Neurotech S.A., Evry (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/173,205

(22) Filed: Oct. 15, 1998

(65) Prior Publication Data

US 2001/0051608 A1 Dec. 13, 2001

Related U.S. Application Data

(63) Continuation of application No. 08/213,668, filed on Mar. 15, 1994, now abandoned.

(51) Int. Cl.[7] .......................... C12N 15/63; A61K 31/70
(52) U.S. Cl. ...................... 435/320.1; 514/44; 424/468; 424/486; 424/484; 424/497; 435/455
(58) Field of Search ......................... 514/44; 435/320.1, 435/455; 424/450, 468, 486, 484, 497

(56) References Cited

U.S. PATENT DOCUMENTS

| | | | |
|---|---|---|---|
| 4,272,398 A | 6/1981 | Jaffe | 252/316 |
| 4,775,624 A | 10/1988 | Bang et al. | 435/226 |
| 4,861,627 A | 8/1989 | Mathiowitz et al. | 427/213.31 |
| 4,863,735 A | * 9/1989 | Kohn et al. | 424/422 |
| 5,100,669 A | 3/1992 | Hyon et al. | 424/426 |
| 5,100,792 A | 3/1992 | Sanford et al. | 435/455 |
| 5,171,217 A | 12/1992 | March et al. | 604/53 |
| 5,271,961 A | 12/1993 | Mathiowitz et al. | 427/213.31 |
| 5,639,473 A | * 6/1997 | Grinstaff et al. | 424/450 |
| 5,643,578 A | * 7/1997 | Robinson et al. | 424/210.1 |
| 5,763,416 A | * 6/1998 | Bonadio et al. | 514/44 |
| 5,820,883 A | * 10/1998 | Tice et al. | 424/501 |

FOREIGN PATENT DOCUMENTS

| | | |
|---|---|---|
| EP | 0 248 531 | * 12/1987 |
| EP | 0 330 180 | * 2/1988 |
| EP | 0 302 582 | * 2/1989 |
| EP | 0579347 A1 | 1/1994 |
| WO | WO 93/08850 | 5/1993 |
| WO | WO 93/21906 | * 11/1993 |
| WO | WO 93/25221 | 12/1993 |
| WO | WO 94/23738 | 10/1994 |

OTHER PUBLICATIONS

Duncan (Anti–Cancer Drugs, 3, pp. 175–210, 1992.*
Clark et al. (eds.) 1988 in: The Molecular and Cellular Biology of Wound Repair (ISBN 0–306–42716–8) pp. 3–33.
Yang, N.–S. 1992 Crit. Rev. Biotechnol. 12, 335–356.
Tai and Sun, "Microencapsulation of recombinant cells: a new delivery system for gene therapy," *The FASEB Journal* 7:1061–1069 (1993).
Benita, S., et al., "Characterization of Drug–Loaded Poly-(d.l–lactide) Microspheres", *J. Pharm. Sci.*, 73:1721–1724 (Dec. 1984).
Blau, H.M., "Muscling in on Gene Therapy", *Nature*, 364:673–675 (1993).
Cohen, J., "Naked DNA Points Way to Vaccines", *Science*, 259:1691–1692 (Mar., 1993).
Salib, N.N., et al., "Utilization of Sodium Alginate in Drug Microencapsulation", *Pharmazeutische Industrie*, 40(11A):1230–1234 (1978).
Sawhney, A.S., et al., "Bioerodible Hydrogels Based on Photopolymerized Poly(ethylene glycol)–co–poly($\alpha$–hydroxy acid) Diacrylate Macromers", *Macromolecules*, 26:581 587 (1993).
Ulmer, J.B., et al., "Heterologous Protection Against Influenza by Injection of DNA Encoding a Viral Protein", *Science*, 259:1745–1749 (Mar., 1993).
Wilson, J.M., "Vehicles for Gene Therapy," *Nature*, 365:691–692 (Oct., 1993).
Wivel, N.A., et al., "Germ–line Gene Modification and Disease Prevention: Some Medical and Ethical Perspectives," *Science*, 262:533–538 (Oct., 1993).
Wolff, J.A., "Human Dystrophin Expression in MDX Mice After Intramuscular Injection of DNA Constructs", *Nature*, 352:815–818 (Mar., 1991).
Wolff, J.A., et al., "Direct Gene Transfer Into Mouse Muscle In Vivo," *Science*, 247:1465–1468 (1990).
Jiao, S., et al., "Persistence of Plasmid DNA and Expression in Rat Brain Cells In Vivo", *Experimental Neurology*, 115:400–413 (1992).

(List continued on next page.)

*Primary Examiner*—Dave T. Nguyen

(57) ABSTRACT

A means for obtaining efficient introduction of exogenous genes into a patient, with long term expression of the gene, is disclosed. The gene, under control of an appropriate promoter for expression in a particular cell type, is encapsulated or dispersed with a biocompatible, preferably biodegradable polymeric matrix, where the gene is able to diffuse out of the matrix over an extended period of time, for example, a period of three to twelve months or longer. The matrix is preferably in the form of a microparticle such as a microsphere (where the gene is dispersed throughout a solid polymeric matrix) or microcapsule (gene is stored in the core of a polymeric shell), a film, an implant, or a coating on a device such as a stent. The size and composition of the polymeric device is selected to result in favorable release kinetics in tissue. The size is also selected according to the method of delivery which is to be used, typically injection or administration of a suspension by aerosol into the nasal and/or pulmonary areas. The matrix composition can be selected to not only have favorable degradation rates, but to be formed of a material which is bioadhesive, to further increase the effectiveness of transfer when administered to a mucosal surface.

8 Claims, No Drawings

OTHER PUBLICATIONS

Kay, M.A., et al., "In Vivo Therapy of Hemophilia B: Sustained Partial Correction in Factor IX–Deficient Dogs", *Science*, 262:117–119 (Oct., 1993).

Lim, F., et al., "Microencapsulation of Living Cells and Tissues", *J. Pharm. Sci.*, 70(4):351–354 (Apr., 1981).

Marx, J., "A First Step Toward Gene Therapy for Hemophilia B", *Science*, 262:29–30 (Oct., 1993).

Mathiowitz, E., et al., "Morphology of Polyanhydride Microsphere Delivery Systems", *Scanning Microscopy*, 4(2):329–340 (1990).

Mathiowitz, E., et al., "Novel Microcapsules for Delivery Systems", *Reactive Polymers*, 6:275–283 (1987).

Mathiowitz, E., et al., "Polyanhydride Microspheres. IV. Morphology and Characterization of Systems Made by Spray Drying", *J. Appl. Polymer Sci.*, 45, 125–134 (1992).

Mathiowitz, E., et al., "Polyanhydride Microspheres as Drug Carriers. II. Microencapsulation by Solvent Removal", *J. Appl. Polymer Sci.*, 35:755–774 (1988).

Mathiowitz, E., et al., "Polyanhydride Microspheres as Drug Carriers: I. Hot–Melt Microencapsulation", *J. Controlled Release*, 5:13–22 (1987).

Mulligan, R.C., "The Basic Science of Gene Therapy", *Science*, 260:926–931 (May, 1993).

Nabel, J.G., et al., "Direct Gene Transfer With DNA–Liposome Complexes in Melanoma: Expression, Biologic Activity and Lack of Toxicity in Humans", *Proc. Nat. Acad. Sci. USA*, 90:11307–11311 (Dec., 1993).

Nicolau, C., et al., "In vivo Expression of Rat Insulin After Intravenous Administration of the Lipsome–Entrapped Gene for Rat Insulin I", *Proc. Natl. Acad. Sci. USA*, 80:1068–1072 (Feb., 1983).

Partridge, T.A., "Muscle Transfection Made Easy," *Nature*, 352:757–758 (Aug., 1991).

Rosenberg., S., et al., "Use of Tumor–Infiltrating Lymphocytes and Interleukin–2 in the Immunotherapy of Patients with Metastatic Melanoma", A Preliminary report, *New England J. Med.*, 319:1676–1680 (Dec., 1988).

* cited by examiner

POLYMERIC GENE DELIVERY

This application is a continuation application under 37 §1.53(b) of U.S. Ser. No. 08/213,668, filed on Mar. 15, 1994 now abandoned, incorporated herein by reference.

BACKGROUND OF THE INVENTION

The present invention is generally in the area of drug delivery devices and is specifically in the area of polymeric drug delivery devices.

Gene therapy is generally defined as the introduction and expression of an exogenous gene in an animal to supplement or replace a defective or missing gene. Examples that have received a great deal of recent attention include the genes missing in cystic fibrosis and severe combined immunodeficiency. Although tremendous progress has been made in the area of gene therapy, obtaining long term expression of the desired proteins remains elusive.

In the majority of cases, a retroviral vector is used to introduce the gene to be expressed into appropriate cells. Gene transfer is most commonly achieved through a cell-mediated ex vivo therapy in which cells from the blood or tissue are genetically modified in the laboratory and subsequently returned to the patient. The clinical studies by Steven Rosenberg, et al., "Immunotherapy of patients with metastatic melanoma using tumor-infiltrating lymphocytes and IL-2", Preliminary report, *New England J. Med.,* 319 (1988) 1676–1680, using in vitro-activated LAK and TIL for tumor destruction illustrates this approach. In other cases, the vector carrying the gene to be expressed is introduced into the patient, for example, by inhalation into the lungs in the case of cystic fibrosis. Transfected cells have also been implanted, alone or encapsulated within a protective membrane that protects the cells from the inflammatory response of the body while at the same time allowing the gene product to diffuse out of the membrane. There have also been reports of the direct injection of an exogenous gene in combination with an appropriate promoter, into tissue, with some transient expression being noted.

Viral vectors have been widely used in gene transfer, due to the relatively high efficiency of transfection and potential long term effect through the actual integration into the host's genome. However, there are still concerns about the risks involved in the use of viruses. Activation of proto-oncogenes and reversion to wild-type viruses from replication incompetent viruses are some important potential hazards of viral delivery of genes.

Since the discovery that naked DNA is taken up by muscle cells and transiently expressed in vivo, and subsequent reports, by Woeff, Jon A et al., "Direct gene transfer into mouse muscle in vivo," *Science,* 247, 1465–1468, 1990; and Ascadi et al., "Human dystrophin expression in mdx mice after intramuscular injection of DNA constructs," *Nature,* 352, 815–818, 1991, there has been increasing interest in using non-viral vehicles for in vivo transfections.

Plasmid DNA, which can function episomally, has been used with liposome encapsulation, $CaPO_4$ precipitation and electroporation as an alternative to viral transfections. Recent clinical trials with liposome encapsulated DNA in treating melanoma illustrates this approach to gene therapy, as reported by Nabel, J. G., et al., "Direct gene transfer with DNA-liposome complexes in melanoma: Expression, biological activity and lack of toxicity in humans", *Proc. Nat. Acad. Sci. U.S.A.,* 90 (1993) 11307–11311. A foreign gene coding for HLA-B was introduced into subcutaneous sites of melanoma tumors. Expression of the new gene and the absence of an anti-DNA host response was confirmed. Wolff, Jon A, "Persistence of plasmid DNA and expression in rat brain cells in vivo," *Experimental Neurology,* 115, 400–413, 1992, also reported expression of plasmid DNA. Thus, direct gene transfer offers the potential to introduce DNA encoding proteins to treat human diseases.

The mechanisms for cellular uptake of exogenous DNA and subsequent expression are not clear but gene transfer with naked DNA is associated with several characteristics. Unlike in the case of oligonucleotides, which are typically a maximum of twenty to thirty nucleotides in length, genes encoding most molecules of therapeutic interest are quite large, and therefore considerably more difficult to introduce into cells other than through retroviral vector, or in vitro, by chemical manipulation, so that the efficiency of transfer is low. In most reported cases to date, only transient expression of up to a few weeks or months has been observed. Although low level expression and short term expression are two important drawbacks with direct DNA transfer, transfections with naked DNA have several advantages over viral transfers. Most importantly, concerns related to the immunogenicity and transforming capability of viruses are avoided. In addition, naked DNA is easy to produce in large quantities, is inexpensive, and can be injected at high concentration into localized tissue sites allowing gene expression in situ without extensive ex vivo therapy.

The following additional articles review the current state of gene therapy and the problems associated therewith: Blau, Helen M, "Muscling in on gene therapy," *Nature,* 364, 673–675, 1993; Cohen, Jon, "Naked DNA points way to vaccines," *Science,* 259, 1691–1692, 1993; Dagani, Ron, "*Gene* therapy advance, anti-HIV antibodies work inside cells," *C&EN,* 3–4, 1993; Felgner, Philip L, "Lipofectamine reagent: A new, higher efficiency polycationic liposome transfection reagent," *Focus/Gibco,* 15, 73–78, 1993; Liu, Margaret A et al, "Heterologous protection against influenza by injection of DNA encoding a viral protein," *Science,* 259, 1745–1749, 1993; Marx, Jean, "A first step toward gene therapy for hemophilia B," *Science,* 262, 29–30, 1993; Mulligan, Richard C, "The basic science of gene therapy," *Science,* 260, 926–931, 1993; Nicolau, Claude, et al., "In vivo expression of rat insulin after intravenous administration of the liposome-entrapped gene for rat insulin I," *Proc. Natl. Acad. Sci. USA,* 80, 1068–1072, 1983; Partridge, Terence A, "Muscle transfection made easy," *Nature,* 352, 757–758, 1991; Wilson, James M, "Vehicles for gene therapy," *Nature,* 365, 691–692, 1993; Wivel, et al., "Germ-line gene modification and disease prevention: Some medical and ethical perspectives," *Science,* 262, 533–538, 1993; and Woo, Savio L C et al., "In vivo gene therapy of hemophilia B: sustained partial correction in Factor IX-deficient dogs," *Science,* 262, 117–119, 1993.

Gene therapy is one of the most promising areas of research today. It would therefore be extremely useful if one had an efficient way to introduce genes into cells which yielded long term expression.

It is therefore an object of the present invention to provide a means for efficient transfer of exogenous genes to cells in a patient.

It is a further object of the present invention to provide a means for long term expression of exogenous genes in patients.

It is a further object of the present invention to provide a means for increasing or decreasing the inflammatory response to implanted polymeric devices.

It is a still further object of the present invention to provide a method for immunization of individuals over a more prolonged period of time than is achieved by a single or multiple immunization protocol.

It is another object of the present invention to provide a method for targeting of gene delivery either to tissue cells or to inflammatory type cells.

SUMMARY OF THE INVENTION

A means for obtaining efficient introduction of exogenous genes into a patient, with long term expression of the gene, is disclosed. The gene, under control of an appropriate promoter for expression in a particular cell type, is encapsulated or dispersed with a biocompatible, preferably biodegradable polymeric matrix, where the gene is able to diffuse out of the matrix over an extended period of time, for example, a period of three to twelve months or longer. The matrix is preferably in the form of a microparticle such as a microsphere (where the gene is dispersed throughout a solid polymeric matrix) or microcapsule (gene is stored in the core of a polymeric shell), although other forms including films, coatings, gels, implants, and stents can also be used. The size and composition of the polymeric device is selected to result in favorable release kinetics in tissue. The size is also selected according to the method of delivery which is to be used, typically injection into a tissue or administration of a suspension by aerosol into the nasal and/or pulmonary areas. The matrix composition can be selected to not only have favorable degradation rates, but to be formed of a material which is bioadhesive, to further increase the effectiveness of transfer when administered to a mucosal surface, or selected not to degrade but to release by diffusion over an extended period.

Examples demonstrate the effectiveness of the system in animals.

DETAILED DESCRIPTION OF THE INVENTION

Gene transfer is achieved using a polymeric delivery system which releases entrapped genes, usually in combination with an appropriate promoter for expression of the gene, into surrounding tissue. Efficacy of transfer is achieved by: a) releasing the gene for prolonged period of time, b) minimizing diffusion of the gene out of the delivery system (due to its size) so that release is predominantly degradation dependent, and c) improving the transient time of expression and the low infection seen by direct gene therapy. In case of non-erodible polymers, the device is formulated so that the gene is released via diffusion. This is achieved by creating porous systems or adding soluble bulking agents that create pores as they leach out of the system.

The Polymeric Matrices

Selection of Polymer

Both non-biodegradable and biodegradable matrices can be used for delivery of genes, although biodegradable matrices are preferred. These may be natural or synthetic polymers, although synthetic polymers are preferred due to the better characterization of degradation and release profiles. The polymer is selected based on the period over which release is desired, generally in the range of at least three months to twelve months, although longer periods may be desirable. In some cases linear release may be most useful, although in others a pulse release or "bulk release" may provided more effective results. The polymer may be in the form of a hydrogel (typically in absorbing up to about 90% by weight of water), and can optionally be crosslinked with multivalent ions or polymers.

High molecular weight genes can be delivered partially by diffusion but mainly by degradation of the polymeric system. In this case, biodegradable polymers, bioerodible hydrogels, and protein delivery systems are particularly preferred. Representative synthetic polymers are: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellullose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly (lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in *Macromolecules*, 1993, 26, 581–587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Selection of Matrix Form and Size

In the preferred embodiment, the polymeric matrix is a microparticle between nanometers and one millimeter in diameter, more preferably between 0.5 and 100 microns for administration via injection or inhalation (aerosol).

The microparticles can be microspheres, where gene is dispersed within a solid polymeric matrix, or microcapsules, where the core is of a different material than the polymeric shell, and the gene is dispersed or suspended in the core, which may be liquid or solid in nature. Unless specifically defined herein, microparticles, microspheres, and microcapsules are used interchangeably.

Alternatively, the polymer may be cast as a thin slab or film, ranging from nanometers to four centimeters, a powder produced by grinding or other standard techniques, or even a gel such as a hydrogel. The polymer can also be in the form of a coating or part of a stent or catheter, vascular graft, or other prosthetic device.

Methods for Making the Matrix

The matrices can be formed by solvent evaporation, spray drying, solvent extraction and other methods known to those skilled in the art.

Microsphere Preparation

Bioerodible microspheres can be prepared using any of the methods developed for making microspheres for drug delivery, for example, as described by Mathiowitz and Langer, *J. Controlled Release* 5,13–22 (1987); Mathiowitz, et al., *Reactive Polymers* 6, 275–283 (1987); and Mathiowitz, et al., *J. Appl. Polymer Sci.* 35, 755–774 (1988), the teachings of which are incorporated herein. The selection of the method depends on the polymer selection, the size, external morphology, and crystallinity that is desired, as described, for example, by Mathiowitz, et al., *Scanning Microscopy* 4,329–340 (1990); Mathiowitz, et al., *J. Appl. Polymer Sci.* 45, 125–134 (1992); and Benita, et al., *J. Pharm. Sci.* 73, 1721–1724 (1984), the teachings of which are incorporated herein.

In solvent evaporation, described for example, in Mathiowitz, et al., (1990), Benita, and U.S. Pat. No. 4,272, 398 to Jaffe, the polymer is dissolved in a volatile organic solvent. The DNA, either in soluble form or dispersed as fine particles, is added to the polymer solution, and the mixture is suspended in an aqueous phase that contains a surface active agent such as poly(vinyl alcohol). The resulting emulsion is stirred until most of the organic solvent evaporates, leaving solid microspheres.

In general, the polymer can be dissolved in methylene chloride. Several different polymer concentrations can be used, for example, between 0.05 and 0.20 g/ml. After loading the solution with DNA, the solution is suspended in 200 ml of vigorously stirring distilled water containing 1% (w/v) poly(vinyl alcohol) (Sigma Chemical Co., St. Louis, Mo.). After four hours of stirring, the organic solvent will have evaporated from the polymer, and the resulting microspheres will be washed with water and dried overnight in a lyophilizer.

Microspheres with different sizes (1–1000 microns) and morphologies can be obtained by this method which is useful for relatively stable polymers such as polyesters and polystyrene. However, labile polymers such as polyanhydrides may degrade due to exposure to water. For these polymers, hot melt encapsulation and solvent removal may be preferred.

In hot melt encapsulation, the polymer is first melted and then mixed with the solid particles of DNA, preferably sieved to less than 50 $\mu$m. The mixture is suspended in a non-miscible solvent such as silicon oil and, with continuous stirring, heated to 5° C. above the melting point of the polymer. Once the emulsion is stabilized, it is cooled until the polymer particles solidify. The resulting microspheres are washed by decantation with petroleum ether to give a free-flowing powder. Microspheres with diameters between one and 1000 microns can be obtained with this method. The external surface of spheres prepared with this technique are usually smooth and dense. This procedure is useful with water labile polymers, but is limited to use with polymers with molecular weights between 1000 and 50000.

Solvent removal was primarily designed for use with polyanhydrides. In this method, the drug is dispersed or dissolved in a solution of a selected polymer in a volatile organic solvent like methylene chloride. The mixture is then suspended in oil, such as silicon oil, by stirring, to form an emulsion. Within 24 hours, the solvent diffuses into the oil phase and the emulsion droplets harden into solid polymer microspheres. Unlike solvent evaporation, this method can be used to make microspheres from polymers with high melting points and a wide range of molecular weights. Microspheres having a diameter between one and 300 microns can be obtained with this procedure. The external morphology of the spheres is highly dependent on the type of polymer used.

In spray drying, the polymer is dissolved in methylene chloride (0.04 g/ml). A known amount of active drug is suspended (if insoluble) or co-dissolved (if soluble) in the polymer solution. The solution or the dispersion is then spray-dried. Typical process parameters for a mini-spray drier are as follows: polymer concentration=0.04 g/ml, inlet temperature=24° C., outlet temperature=13 to 15° C., aspirator setting=15, pump setting=10 ml/min, spray flow=600 NLh$^{-1}$, and nozzle diameter=0.5 mm. Microspheres ranging in diameter between one and ten microns can be obtained with a morphology which depends on the selection of polymer.

Double walled microspheres can be prepared according to U.S. Pat. No. 4,861,627 to Mathiowitz.

Hydrogel microspheres made of gel-type polymers such as alginate or polyphosphazines or other dicarboxylic polymers can be prepared by dissolving the polymer in an aqueous solution, suspending the material to be incorporated into the mixture, and extruding the polymer mixture through a microdroplet forming device, equipped with a nitrogen gas jet. The resulting microspheres fall into a slowly stirring, ionic hardening bath, as described, for example, by Salib, et al., *Pharmazeutische Industrie* 40-11A, 1230 (1978), the teachings of which are incorporated herein. The advantage of this system is the ability to further modify the surface of the microspheres by coating them with polycationic polymers such as polylysine, after fabrication, for example, as described by Lim, et al., *J. Pharm. Sci.* 70, 351–354 (1981). For example, in the case of alginate, a hydrogel can be formed by tonically crosslinking the alginate with calcium ions, then crosslinking the outer surface of the microparticle with a polycation such as polylysine, after fabrication. The microsphere particle size will be controlled using various size extruders, polymer flow rates and gas flow rates.

Chitosan microspheres can be prepared by dissolving the polymer in acidic solution and crosslinking with tripolyphosphate. For example, carboxymethylcellulose (CMC) microsphere are prepared by dissolving the polymer in an acid solution and precipitating the microspheres with lead ions. Alginate/polyethylene imide (PEI) can be prepared to reduce the amount of carboxyl groups on the alginate microcapsules. Table 1 summarizes various hydrogels, concentrations, ionic baths, and stirring rates used to manufacture them.

TABLE 1

Preparation of Hydrogel Matrices

| Hydrogel | Hydrogel concen. | dissolving bath pH | Temp °C. | ionic bath concen. (w/v) | stirring rate |
|---|---|---|---|---|---|
| chitosan | 1.0% | 5.0 | 23° C. | 3% tripoly-phosphate | 170 rpm |
| alginate | 2.0% | 7.4 | 50° C. | 1.3% calcium chloride | 160 rpm |
| alginate/ PEI | 2.0%/ 6.0% | 7.4 7.4 | 50° C. 50° C. | 1.3% calcium chloride | 160 rpm |
| Carboxy methyl cellulose | 2.0% | 7.4 | 50° C. | 10.0% lead nitrate | 100 rpm |

Other Device Forms

Other delivery systems including films, coatings, pellets, slabs, and devices can be fabricated using solvent or melt casting, and extrusion, as well as standard methods for making composites. The polymer can be produced by first mixing monomers and DNA as described by Sawhney, et al., and polymerizing the monomers with UV light. The polymerization can be carried out in vitro as well as in vivo. Thus, any biocompatible glue could be also used to incorporate the DNA.

Loading of Gene

The range of loading of the gene to be delivered is typically between about 0.01% and 90%, depending on the form and size of the gene to be delivered and the target tissue.

Selection of Genes to be Incorporated

Any genes that would be useful in replacing or supplementing a desired function, or achieving a desired effect such as the inhibition of tumor growth, could be introduced using the matrices described herein. As used herein, a "gene" is an isolated nucleic acid molecule of greater than thirty nucleotides, preferably one hundred nucleotides or more, in length.

Examples of genes which replace or supplement function include the genes encoding missing enzymes such as adenosine deaminase (ADA) which has been used in clinical trials to treat ADA deficiency and cofactors such as insulin and coagulation factor VIII.

Genes which effect regulation can also be administered, alone or in combination with a gene supplementing or replacing a specific function. For example, a gene encoding a protein which suppresses expression of a particular protein-encoding gene, or vice versa, which induces expresses of a protein-encoding gene, can be administered in the matrix.

Examples of genes which are useful in stimulation of the immune response include viral antigens and tumor antigens, as well as cytokines (tumor necrosis factor) and inducers of cytokines (endotoxin), and various pharmacological agents.

The chronic immune response to the polymeric matrix is mediated by the action of a variety of growth factors including epidermal growth factor (EGF), platelet-derived growth factor (PDGF), fibroblast growth factors (FGFs), transforming growth factors (TGF-$\alpha$ and TGF-$\beta$, interleukin-1 (IL-1), and tumor necrosis factor (TNF). Inhibitors of these inflammatory mediators in combination with a gene to be delivered other than the immune inhibitor would be effective in decreasing the normal inflammatory response directed toward the polymeric matrix. By inhibiting the amount of encapsulation of the matrix, the effective release would be further extended. Examples of materials which could inhibit encapsulation include antisense mRNA to suppress fibrin or collagen formation, inhibitors of EGF, PDGF, FGFs, TGF-$\alpha$, TGF-$\beta$, IL-1 and TNF and anti-inflammatory agents such as corticosteroids and cyclosporin.

Genes can be obtained using literature references or from commercial suppliers. They can be synthesized using solid phase synthesis if relatively small, or obtained in expression vectors, for example, as deposited with the American Type Culture Collection, Rockville, Md.

Selection of Vectors to be Introduced in Combination with the Gene

As used herein, vectors are agents that transport the gene into the cell without degradation and include a promoter yielding expression of the gene in the cells into which it is delivered. Promoters can be general promoters, yielding expression in a variety of mammalian cells, or cell specific, or even nuclear versus cytoplasmic specific. These are known to those skilled in the art and can be constructed using standard molecular biology protocols. Although as demonstrated by the examples, the genes will diffuse out of the polymeric matrix into the surrounding cells where they are expressed, in a preferred embodiment, the genes are delivered in combination with a vector to further enhance uptake and expression. Vectors are divided into two classes:
 a) Biological agents derived from viral, bacterial or other sources.
 b) Chemical/physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells.

Retroviral vectors are the vectors most commonly used in clinical trials, since they carry a larger genetic payload than other viral vectors. However, they are not useful in non-proliferating cells.

Adenovirus vectors are relatively stable and easy to work with, have high titers, and can be delivered in aerosol formulation. However, many people may have pre-existing antibodies negating effectiveness and they are difficult to produce in quantity.

Pox viral vectors are large and have several sites for inserting genes, they are thermostable and can be stored at room temperature. However, they cannot be transmitted from host to host and there are some safety issues since they can enter other cells.

Plasmids are not integrated into the genome and their life span is from few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. The chemical/physical methods have a number of problems, however, and will typically not be used with the polymeric matrices described herein. For example, chemicals mediators are impractical for in vivo use: when calcium phosphate is used there appears to be very low transduction rate, when sodium butyrate is used the inserted gene is highly unstable and when glycerol is used inserted gene is rapidly lost.

Pharmaceutical Compositions

The microparticles can be suspended in any appropriate pharmaceutical carrier, such as saline, for administration to a patient. In the most preferred embodiment, the microparticles will be stored in dry or lyophilized form until immediately before administration. They will then be suspended in sufficient solution for administration.

In some cases, it may be desirable to administer the microparticles in combination with an adjuvant to enhance the inflammatory response against the polymer and thereby increase the likelihood of phagocytosis by macrophages and other hematopoietic cells, with subsequent expression of the gene specifically within these cells, or, in the case where the microparticles contain an anti-cancer agent, to enhance the inflammatory reaction against the tumor cells in combination with the effect of the anti-cancer agent.

The polymeric microparticles can be administered by injection, infusion, implantation, orally (not preferred), or administration to a mucosal surface, for example, the nasalpharyngeal region and/or lungs using an aerosol, or in a cream, ointment, spray, or other topical carrier, for example, to rectal or vaginal areas. The other devices are preferably administered by implantation in the area where release is desired.

The materials can also be incorporated into an appropriate vehicle for transdermal delivery as well as stents. Appropriate vehicles include ointments, lotions, patches, and other standard delivery means. Targeting of cell populations through polymer material characteristics.

Studies with plasmid release using PLA/PCL biodegradable polymers indicate that the majority of transfected cells, assessed with the β-galactosidase reporter gene, are inflammatory cells involved in the "foreign body" response. In general, non-degrading polymers evoke a stronger inflammatory response when compared to non-biodegrading polymers. A strong foreign body response results in a thick layer of macrophages, fibroblasts, and lymphocytes around the implant. Because the polymer release device relies on diffusion for movement of its particles, a strong inflammatory response will limit the effective distance of diffusion. Accordingly, biodegrading polymers can be used to target inflammatory cells due to the inability of the plasmid DNA (pDNA) to migrate across the reactive tissue layer to the site specific tissue. A more biocompatible material which induces a weaker response from the host will result in a thinner layer of inflammatory cells, enabling the released pDNA to migrate across the inflammatory cells to the indigenous cells to be transfected.

Incorporation of Antiinflammatories and Immune Enhancers; Treatment of Cancers

In recent years, considerable attention has been focused on the use of gene therapy to treat various diseases including cancer. Generally, gene therapy for cancer therapeutics either targets the cells of the immune system to enhance their ability to kill malignant cells or directly targets the cancer cells to regulate their proliferation or enhance some cellular function which will result in a stronger activation of the immune response.

Most types of cancer are characterized by frequent relapses during the course of treatment and the continued non-specific and/or specific activation of the immune system resulting from gene therapy is crucial. Second, cell targeting is a major limitation of current vectors and implantation of a controlled release device directly inside a tumor where the DNA is released locally is one alternative to ex vivo therapy or the development of effective ligand specific vectors. As indicated by the prevalence of ex vivo therapy, targeting hematopoietic cells is especially difficult. The histological results from the implant site in the studies described in the examples below, reveal a substantial inflammatory response surrounding the intramuscular implant. The well known "foreign body" host response can be used to an advantage as this migration of lymphocytes and antigen presenting cells raises the possibility of directing the transfection to these specific cell populations.

Tumors elicit both the humoral and cell-mediated immune response, and lymphocytes, particularly cytotoxic T cells and NK cells, as well as macrophages, are known to play a crucial role in tumor elimination. Gene therapy for cancer treatment either targets these cells or the malignant cells themselves. An implant releasing naked DNA for long term functional gene transfer which can target inflammatory cells and/or tumor cells could significantly improve cancer therapy.

The approaches used include upregulation of class I MHC expression, transduction of antigen presenting cells with tumor-specific antigens, cytokine immunotherapy, transfection of tumor cells with tumor suppressor genes and antisense therapy.

The malignant transformation of cells is often characterized by a reduction of class I MHC expression leading to a severe depression of the CTL-mediated immune response. An increase in class I MHC expression on tumor cells could facilitate the activation of the immune system against these altered self-cells. Transfection of genes for cytokines such as tumor necrosis factor (TNF) into tumor cells or tumor suppressor genes such as p53 can be used to limit the ability of tumor cells to multiply. Anti-sense therapy targets cell proliferation or the production of necessary proteins such as tumor angiogenesis factor (TAF) by complementary RNA hybridization to block transcription of specific genes.

The immune system can be activated and induced to attack specific cells using cytokines such as Proleukin or monoclonal antibodies. For example, cancer cells proliferate in part due to a decreased immune response against the transformed cells. The matrices described herein provide a means to allow recognition and provocation of a response to cancer cells. For example, genes coding for antigens; such as the aberrant epithelial mucin of breast cancer, and monoclonal antibodies directed against tumor antigens have been shown to have potential in stimulating immune destruction of malignant cells. These genes, alone or in combination with monoclonal antibodies, can be delivered to the tumor sites in the polymeric matrices to achieve inhibition of the tumor cells.

Cancer cells can also be treated by introducing chemotherapy drug resistant genes into healthy cells to protect them against the toxicity of drug therapy, or by the insertion of appropriate vectors containing cytotoxic genes or blocking genes into a tumor mass to eliminate cancer cells. In a preferred embodiment, the immune system is specifically stimulated against antigens or proteins on the surface of the cancer cells.

These approaches can be used in vitro and in vivo. In vitro, the cells can be removed from a patient, the gene inserted into the cell and the cells reintroduced into the patient. In vivo, the gene can be directly introduced into the body either systematically or in localized sites.

Another approach is to use suicide genes that cause cell death when they are activated or when their product is combined with a pharmaceutical. The primary limitation of the method is the fact that the gene should be targeted to the cancer cell and not to normal cell. Current approach to overcome the problem is direct injection of the vectors into a localized area where normal cells do not proliferate. This would be greatly facilitated using the polymeric devices described herein. The advantages of polymeric devices in this setting include continuous and protracted release of the incorporated pharmaceutical. This increases the liklihood that the intended purposes, for example, treatment of cancerous cells, will be achieved.

EXAMPLES

The method and materials of the present invention will be further understood by reference to the following non-limiting examples.

Example 1

Expression of Linear and Supercoiled Plasmid DNA Encapsulated in Polymeric Implants in Muscle Tissue of Rats The study described in this example confirms the feasibility of in vivo transfections using biodegradable polyester blends to release linear or supercoiled plasmid DNA. Although only short term expression was studied in this study, polymer devices releasing drugs offer the potential for sustained long term delivery of naked DNA.

Marker genes are used to study the movement of engineered cells containing exogenous genes, as well as the vectors and genes introduced with the vectors, to insure that the genes remain where they are introduced. Almost all of the initial research into gene therapy is with marker genes. Preferred marker genes are those whose product is innocuous and which can be readily detected by simple laboratory tools. An appropriate marker gene is β-galactosidase (β-gal), since expression is readily detected by addition of X-gal, a substrate which yields a blue color when the active enzyme is present.

Encapsulation of Linear and Supercoiled β-gal Coding DNA in a PLA Blend 1 g polyactic acid (PLA) (300K) and 2 g PLA (2K) was dissolved in 10 ml of methylene chloride and 5 drops of (SPAN ™) 85. The mixture was divided into two aliquots of 5 ml and 100 ul of either circular or linear DNA (between 1 and 2 mg/ml diluted 1:5 in buffer) was introduced into the aliquots. Each mixture was mixed well and aliquoted into glass vials (1 ml/vial). Between 20 μg and 40 μg of β-gal plasmid DNA was encapsulated in each glass vial. The glass vials were left in the refrigerator for four days to evaporate the methylene chloride and then lyophilized.

Implantation of DNA/PLA pellets

Each sample was first sterilized with ethanol for 5 min and then washed with PBS-penicillin/streptomycin for 5 min. Surgery was done on Sprague Dawley rats. Linear DNA was implanted into the left leg and supercoiled DNA implanted into the right. Implants were inserted into incised muscle— either in the vastus or the hamstring. The muscle was sutured back together and then the skin was sutured closed. Rats were sacrificed for analysis at two weeks.

Results

Rats were perfused with Phosphate Buffered Saline (PBS) with 2500 units of heparin followed by 3% paraformaldehyde and 0.2% glutaraldehyde in PBS. The tissue was post-fixed with 3% paraformaldehyde followed by 15% sucrose/PBS. Excised muscles were cut with a cryostat and stained with X-gal.

Histology of the implant sites revealed a substantial inflammatory response around the film at two weeks and two months. The bulk of the β-gal positive staining was localized to this area with few muscle cells exhibiting positive staining. The cells present around the implant probably consists of phagocytic cells, lymphocytes and fibroblasts. As expected, transfection was more efficient with supercoiled DNA.

Example 2

In vitro transfection with pRSV β-gal

NIH3T3 fibroblasts were plated onto a 6 well tissue culture dish with 1 ml of D-MEM (10% Fetal calf serum with penicillin/streptomycin). 24 hours after plating, the cells were transfected with pRSV β-gal control plasmids as per Promega Profection Mammalian

| Transfection system. | |
| --- | --- |
| Plate 1: | 10 μl pRSV-Z (3.4 μg) Calcium Phosphate Precipitated |
| Plate 2: | 30 μl pRSV-Z (10.2 μg) Calcium Phosphate Precipitated |
| Plate 3: | 10 μl pRSV-Z (3.4 μg) Naked DNA |
| Plate 4: | 30 μl pRSV-Z (10.2 μg) Naked DNA |
| Plate 5: | DNA/PLA |
| Plate 6: | Control |

Plate 5 with the PLA pellet was placed into the well with 4 ml of media to counter the effect of the decrease in pH. After 24 hours, the DNA/PLA pellet was removed and the media left unchanged. At 48 hours, the cells were fixed and stained with X-Gal (1 ml/plate) overnight.

Results

The efficiency of transfection was very low. All plates except the control well had a handfull of blue staining cells. There was no observable differences in the number of blue cells among the 5 plates. It was interesting to note that the plate with the DNA/PLA had similar levels of staining as the other plates even after the fact that half the cells had died and detached due to the PLA degradation.

Example 3

Duration of Expression with pSV β-gal DNA Encapsulated Into PLA Blends

In vitro release of plasmid DNA pSV β-gal was amplified in HB101 and purified with Qiagen's MEGA PREP™ 500 μl of plasmid in Tris-EDTA buffer (67.5 µg) was lyophilized and resuspended into 100 µl of sterile dH$_2$O and incorporated into PLA. 0.05 g PLA (2K) and 0.05 g (300K) was dissolved in 1 ml of methylene chloride and 1 drop of SPAN™ 85. After the polymer was in solution, 100 µl of plasmid (67.5 µg) was added to the mixture and vortexed for 15 sec. The resulting film was left in a refrigerator overnight and subsequently lyophilized overnight.

This film was incubated with 1.0 ml of TE buffer at 37° C. under gentle agitation and sample supernatants tested at 24 hours and at 4 days for the presence of released DNA. DNA was assayed by agarose gel electrophoresis on the supernatants.

The results based on the gel of the supernatant after 24 hours of incubation show that a substantial amount of plasmid was released. After 4 days, the results indicate that there was a first phase of release due to the diffusion of plasmid molecules which are close to the surface of the device followed by a slower release at 4 days due to the low degradation rate of the polymer which was too low to be measured.

In vivo transfection levels 3 mg PLA (2K) and 1 mg PLA (100K) were dissolved in methylene chloride (0.25 ml). 1 drop of Span™ 85 and 20 µl of plasmid (20 µg) was added to the solution and homogenized for 1 minute. This solution was air dried in a glass vial for 3 hours in a sterile hood. The brittle film was ground into fine granules and pressed into a pellet form. Three of these DNA containing pellets were made as well as three control pellets without DNA. All pellets were lyophilized overnight to extract residual solvents.

Three rats received DNA/PLA in their left hamstring and control/PLA in their right hamstring. Pellets were inserted into incised hamstrings and the muscles closed with 6-0 Vicryl. Three rats received an injection of pSV β-gal plasmids (20 µg in 100 µl of TE buffer) over a minute long period in their left leg and 100 µl of plain TE buffer in their right leg as controls. The site of injection was marked with suture.

| Rat ID | Left | Right | Implant Duration |
|--------|------|-------|------------------|
| R112 | DNA/PLA | Control/DNA | 1 week |
| R110 | DNA/PLA | Control/DNA | 5 weeks |
| R111 | DNA/PLA | Control/DNA | 10 weeks |
| R115 | DNA/buffer | Control/buffer | 1 week |
| R114 | DNA/buffer | Control/buffer | 5 weeks |

Rats were perfused with PBS/heparin, followed by 4% paraformaldehyde, and post-fixed in 4% paraformaldehyde followed by 15% and 25% sucrose/PBS. Excised muscles were cut with a cryostat and stained with X-Gal.

Results

In vitro release studies indicate that plasmid DNA can be incorporated into polymers without degradation through manufacturing processes and released in functional form for possible uptake by surrounding cells.

In vivo studies reveal that with a 20 µg loading of DNA into the polymer, there is substantial transfection of inflammatory cells at 1 and 5 weeks as confirmed by X-gal staining and immunoblotting. At 10 weeks, there was no difference in staining intensity between the control PLA and DNA/PLA. This is believed to be due to the result of the low loading (20 µg) of the polymer such that after one week the release rate was below half maximal levels. Investigators using direct injection use doses in the 100 µg range to see their effects. A higher initial loading, which will lead to continued release of higher amounts of DNA from polymers, should prolong transfection durations. Rats injected with 20 µg of DNA in solution showed no transfection at 1 and 5 weeks.

Example 4

Comparison of Plasmid DNA Release From Biodegradable and Non-degrading Polymers

Release of plasmids from biodegradable and non-degradable polymer was compared to test the feasibility of targeting either inflammatory cells or tissue specific cells by selection of polymer material. Plasmid DNA was incorporated into a non-degradable elastomer, ethylene vinyl acetate copolymer (EVAc) and implanted into the same site in different animals as PLA/PCL implants. EVAc is a very biocompatible polymer which can be manufactured into a microporous structure through which DNA can diffuse into the surrounding tissue.

Encapsulation of pRSV β-gal into Polymers pRSV β-gal in HB101 was purchased from the ATCC (American Type Culture Collection, Rockville, Md.). The plasmids were grown and purified with Promega's Maxi Prep. 1 ml of a 0.1% solution of ELVAX40 (Dupont) in methylene chloride was vortexed with 645.2 µl of pRSV β-gal (200 µg), frozen in liquid nitrogen and lyophilized. The resulting mixture was extruded at 55° C. into a rod shaped form.

PLA (2K) and polycaprolactone (PLC) (112K) were dissolved in methylene chloride in a 3:1 ratio and 80 mg of the polymer vortexed with 322.6 µl of pRSV β-gal (100 µg). The mixture was left in the refrigerator for 2 days and lyophilized.

Implantation of the Polymers

The EVAc/DNA and PLA/DNA were implanted into rat hamstrings along with their control on opposite sides and sacrificed at 2 weeks.

Results

Histological staining with X-gal reveals positive staining of muscle cells as well as inflammatory cells in close proximity to the EVAc polymeric implant at two weeks post-implantation. In comparison, the PLA/PCL implant reveals positive staining of mostly inflammatory cells only, in accordance with the earlier data regarding biodegradable polymers.

Thus the selection of a biodegradable or non-degradable polymer implant can be used to target delivery to inflammatory cells or tissue cells (for example, muscle). Comparison of PLA/PCL and the EVAc implants illustrates the different transfected cell populations. Specifically, the PLA/PCL implant results in almost exclusive transfection of inflammatory cells while the EVAc implant results in a large number of transfected muscle cells.

Modifications and variations of the method and compositions of the present invention will be obvious to those skilled in the art from the foregoing detailed description. Such modifications and variations are intended to come within the scope of the following claims.

We claim:

1. A preparation of microparticles, each of which preparation of microparticles comprise a synthetic polymeric matrix and an effective amount of naked DNA dispersed within the preparation of microparticles, the polymeric matrix being dissolvable in a volatile organic solvent, wherein
   (a) the size of the microparticles is between 1 and 300 $\mu$m in diameter; and
   (b) the effective amount of naked DNA dispersed within the preparation of microparticles is greater than 20 $\mu$m and wherein the DNA contains a gene operably linked to a promoter, the nucleotide sequence of said gene being greater than 30 nucleotides in length, said naked DNA comprising circular nucleic acid molecules, supercoiled nucleic acid molecules, or a combination of both.

2. The preparation of microparticles according to claim 1 wherein the size of the microparticles is between 1–100 $\mu$m.

3. The preparation of microparticles according to claim 1 wherein the size of the microparticles is between 1–10 $\mu$m.

4. The preparation of microparticles according to any one of claims 1–5 wherein the polymeric matrix is biodegradable.

5. The preparation of microparticles according to any one of claims 1–5 wherein the polymeric matrix is non-biodegradable.

6. The preparation of microparticles according to claim 1 wherein approximately 0.1 –90% by weight of the naked DNA is loaded into the polymeric matrix.

7. The preparation of microparticles of claim 1, wherein the preparation of microparticles contains sufficient entrapped naked DNA such that the naked DNA can be released for three months following implantation.

8. A preparation of microparticles, each of which preparation of microparticles comprises a synthetic polymeric matrix and an effective amount of naked DNA dispersed within the preparation of microparticles, the polymeric matrix being dissolvable in a volatile organic solvent, wherein
   (a) the size of the microparticles is between 1 and 300 $\mu$m in diameter;
   (b) the effective amount of naked DNA dispersed within the preparation of microparticles is greater than 20 $\mu$g and wherein the DNA contains a gene operably linked to a promoter, the nucleotide sequence of said gene being greater than 30 nucleotides in length, said naked DNA comprising circular nucleic acid molecules, supercoiled nucleic acid molecules, or a combination of both; and
   (c) the preparation of microparticles contains sufficient entrapped naked DNA such that the naked DNA can be released for at least 10 weeks following implantation.

* * * * *

UNITED STATES PATENT AND TRADEMARK OFFICE
CERTIFICATE OF CORRECTION

PATENT NO.    : 6,475,779 B2
DATED         : November 5, 2002
INVENTOR(S)   : Edith Mathiowitz et al.

It is certified that error appears in the above-identified patent and that said Letters Patent is hereby corrected as shown below:

<u>Title page,</u>
Item [73], should read -- Brown University Research Foundation, Providence, RI --

Signed and Sealed this

Twelfth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,475,779 B2
DATED : November 5, 2002
INVENTOR(S) : Edith Mathiowitz et al.

It is certified that error appears in the above-identified patent and that said Letters Patent is hereby corrected as shown below:

Column 15,
Line 11, should read -- microparticles is greater than 20 µg --.

Signed and Sealed this

Twenty-fifth Day of November, 2003

JAMES E. ROGAN
*Director of the United States Patent and Trademark Office*